United States Patent [19]

Hummelen et al.

[11] Patent Number: 4,975,380

[45] Date of Patent: Dec. 4, 1990

[54] CHEMILUMINESCENT LABELED ORGANIC REAGENTS AND THEIR USE IN ANALYSIS OF ORGANIC COMPOUNDS

[75] Inventors: Jan C. Hummelen, Groningen; Hans Wynberg, Haren, both of Netherlands

[73] Assignee: Rijksuniversiteit Te Groningen, Groningen, Netherlands

[21] Appl. No.: 445,147

[22] Filed: Nov. 30, 1989

Related U.S. Application Data

[63] Continuation of Ser. No. 285,360, Dec. 14, 1988, abandoned, which is a continuation of Ser. No. 845,129, Dec. 9, 1985, abandoned.

[30] Foreign Application Priority Data

Apr. 16, 1984 [NL] Netherlands .......................... 8401213

[51] Int. Cl.$^5$ .................. C07D 209/38; C07D 209/46; C07D 303/00; G01N 33/533
[52] U.S. Cl. .................................... 436/546; 436/536; 436/800; 548/513; 549/332
[58] Field of Search ....................... 548/513; 549/332; 436/536, 546, 800

[56] References Cited

FOREIGN PATENT DOCUMENTS

WO83/03604 10/1983 PCT Int'l Appl. .

*Primary Examiner*—Christine Nucker
*Assistant Examiner*—Karen I. Krupen
*Attorney, Agent, or Firm*—William M. Blackstone

[57] ABSTRACT

Thermochemically induced luminescence is generated in a fluorescent labeled organic compound containing a covalently bonded fluorescent label which is a polycyclic aromatic radical having at least three linearly fused benzene rings and capable of being excited to a fluorescent electronic excited state by energy transfer from an energy donor molecule or radical having an electronic excited state, by a process comprising generating an energy donor radical or molecule by a thermochemical reaction in the presence of the fluorescent label. The energy donor radical may be generated by a chemical reaction in the presence of the fluorescent labeled organic compound or the fluorescent labeled compound itself may be additionally labeled with a radical capable of being excited to an electronic excited state by a thermochemical reaction, i.e., by a process initiated by adsorption of thermal energy.

35 Claims, No Drawings

CHEMILUMINESCENT LABELED ORGANIC REAGENTS AND THEIR USE IN ANALYSIS OF ORGANIC COMPOUNDS

This is a continuation of application Ser. No. 07,285,360 filed Dec. 14, 1988, abandoned, which is a continuation of application Ser. No. 06,845,129 filed Dec. 9, 1985, abandoned.

FIELD OF THE INVENTION

1. Background of the Invention

This invention relates to organic compounds bearing a luminescent label and more particularly to chemiluminescent labeled organic reagents.

2. Description of the Prior Art

Organic analysis, particularly immunoanalysis, using labeled reagents having a luminescent label has for some time been a useful analytical technique. In practicing this method of analysis a labeled reagent bearing a luminescent, i.e., fluorescent or phosphorescent, label is reacted with an analyte to form a labeled complex. After separation of the complex from the unreacted reagents, the analyte is quantitated by stimulating the label to luminescence, usually by irradiation with light of an appropriate wavelength which when absorbed by the label excited it to a fluorescent or phosphorescent excited state from which it returns to the ground state with emission of detectable radiation. This method of analysis is sensitive and convenient, but it requires the availability of a source of exciting light with which to excite the luminescence of the label.

It is also known to label an organic reagent with a chemiluminescent label which can be excited to a luminescent state by reaction with an added reagent. This procedure does not require a source of exciting light and it offers the possibility of less stray light reaching the luminescence detector. However, it does require an additional chemical step in the analytical procedure.

A further development of luminescent labeled analysis is thermochemiluminescence, wherein the luminescence of the label is excited by the application of heat, ordinarily as the stimulus for a chemical reaction of the label which forms a luminescent excited state. Such a method is described in Dutch patent application No. 8201492, wherein organic compounds are labeled with a 2,2'-epidioxy-2,2'-adamantyladamantane radical or analogue thereof, which will decompose on heating with emission of visible light. The amount of light is proportional to the amount of labeled compound present. This method avoids the necessity for a source of exciting light or for an additional chemical step, since the luminescence is excited simply by heating the compound to be analyzed.

However, it has been found that the efficiency of thermochemiluminescent analysis is rather low because only a small fraction of the label molecules which are excited actually return to the ground state with emission of radiation. The great majority decay by nonradiative processes and so not contribute to the detection of the analyte.

Accordingly, a need has continued to exist for a method of analysis using luminescent labeled reagents analysis with a greater sensitivity.

SUMMARY OF THE INVENTION

It has now been found that thermochemically induced luminescence having greater sensitivity can be carried out using a fluorescent labeled organic compound wherein the molecule to be labeled is bonded by a covalent bond to a polycyclic aromatic radical having at least three linearly fused benzene rings and capable of being excited to a fluorescent electronic excited state by energy transfer from an energy donor molecule or radical having an electronic excited state. The energy donor radical may be generated in the presence of the fluorescent labeled organic compound or the compound itself may be additionally labeled with a radical capable of being excited to an electronic excited state by a thermochemical reaction, i.e., by a process initiated by absorption of thermal energy.

Accordingly, it is an object of the invention to provide organic reagents labeled with fluorescent labels.

A further object is to provide organic reagents having fluorescent labels capable of being excited by energy transfer from excited states of energy donor molecules or radicals.

A further object is to provide organic reagents labeled with a fluorescent label and with an energy donor radical capable of being excited to an electronic excited state by application of heat.

Further objects of the invention will become apparent from the description of the invention which follows.

DETAILED DESCRIPTION OF THE INVENTION AND PREFERRED EMBODIMENTS

The phenomenon of energy transfer from a group or compound in a singlet and/or triplet excited state to a compound capable of being excited to a fluorescent state by energy transfer, is known. According to the invention this phenomenom is used by labeling an organic compound to be assayed with apolycyclic aromatic radical $R_1$, and exciting the radical $R_1$ to a fluorescent state by energy transfer. The radical $R_1$ used in the compounds and method of this invention should be a polycyclic aromatic radical having at least three linearly fused benzene rings. Suitable radicals $R_1$ include radicals derived from rubrene, perylene, 9,10'-dibromoanthracene, 9,10-dichloroanthracene, 9,10-diphenylanthracene, and the like. A particularly preferred radical is that derived from 9,10-diphenylanthracene. The location of the polycyclic aromatic compound which is covalently bonded to the labeled organic molecule is not critical.

When the presence or the amount of an organic compound labeled with one or more radicals $R_1$ is to be determined, the group $R_1$ in the labeled compound is excited to a fluorescent state and the fluorescence is measured. This excitation can be accomplished in one of two ways. In the first method a chemical reaction which generates molecules in singlet and/or triplet excited states is carried out in the presence of a compound labeled with the radical $R_1$. Such a reaction might be, for example, the reaction of a suitable oxalic acid derivative, especially of an oxalic acid ester, with hydrogen peroxide (see Anal. Chem. 55, 432 (1983)), or the decomposition reaction of a dioxetane. Additional chemical reactions of this type include enyzmatic reactions, such as, for example, the oxidation of aliphatic and aromatic aldehydes with peroxidase. In principle, all of the reactions yielding an energy donor, the emission of which shows spectral overlap with the absorption of the acceptor, are suitable.

Another way to excite the label group $R_1$ to a fluorescent state is the use, according to the invention, of organic compounds which in addition to one or more of the $R_1$ label groups, also contain one or more groups $R_2$, which can be excited to a singlet and/or triplet excited state by thermal energy. In this case, the presence or the amount of the so labeled compound can be determined merely by heating the labeled compound and observing the fluorescence. The heating leads to decomposition of the group or groups $R_2$ with generation of groups or compounds in the singlet and/or triplet excited state, which groups or compounds transfer their energy, without radiation, to the group or groups $R_1$. This will cause the group or groups $R_1$ to fluoresce. The emitted fluorescence is proportional to the amount of the labeled compound.

It will be understood by those skilled in the art that the energy donor species may be a molecule, as when the donor is prepared by a chemical reaction in the presence of the fluorescent labeled energy receptor molecule, or a radical, as when the energy donor species is incorporated into the fluorescent labeled compound by a covalent bond. Thus, in this application the term energy donor radical is used to include energy donor molecules as well.

The so labeled organic compounds may be any organic compounds of which it is desired to determine the presence or the amount present. More specifically the labeled organic compounds are substances present in the human or animal body, especially in the body fluids. As such, proteins, steroids or fatty acids may be mentioned, proteins being the most important.

Still more specifically, the present invention is embodied in a protein labeled with one or more groups $R_1$ and, which protein is an immunoreagent, e.g. one of an immunologically complementary pair of reagents. Such immunological pairs consist, for example, of antigens and corresponding antibodies. Further, the labeled organic compound may be an immunological conjugate or complex. If a complex contains one or more groups $R_1$ together with one or more groups $R_2$, $R_1$ may be present in one part of the complex, for example in the antibody part, and $R_2$ in the other part, for example in the corresponding antigen part. Naturally, both groups $R_1$ and $R_2$ may also be present in a single part of the immunological pair.

The polycyclic aromatic group $R_1$ in the labeled compounds according to the invention is, preferably, a 9,10-diphenylanthracyl group. This group very efficiently absorbs energy from a compound in a singlet excited state having an energy level with respect to the ground state of more than about 70 kcal per mole. This energy transfer excites the diphenylanthracyl group to the excited singlet state and the group will fluoresce by returning to the ground state. The diphenylanthracyl group undergoes a radiative fluorescent transition to the ground state with an efficiency of 0.9, and this figure is practically independent of temperature.

The group $R_2$ which is optionally present in the labeled organic compounds according to the invention, preferably corresponds to formula 1,

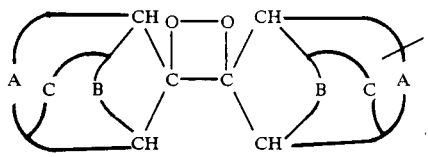

1 in which A and B represent alkylene radicals which may be connected to each other via an optional alkylene radical C. Examples of such radicals $R_2$ are the 2,2'-epidioxy-2,2'-adamantyl-adamant-4-eq.-yl radical, the 9,9'-epidioxy-9,9'-bicyclo[3,3,1]-nonylbicyclo[3,3,1]non-4-eq.-yl radical, the 8,8'-epidioxy-8,8'-bicyclo[3,2,1]-oct-2-yl or -7-yl radical, and the 10,10'-epidioxy-10,10'-bicyclo[4,3,1]-decyl-bicyclo[4,3,1]-deo-2-yl or -7-yl radical. Generally, the alkylene radical A in the group of formula 1 contains 2-5 carbon atoms, alkylene radical B contains 2-5 carbon atoms and alkylene radical C, if present, contains 1-4 carbon atoms. Preferably, the group $R_2$ in the labeled compounds according to the invention is the 2,2'-epidioxy-2,2'-adamantyl-adamant-4-eq.-yl radical.

As mentioned above, the invention also relates to a process for determination or assay of an organic compound labeled with one or more of the above-defined groups $R_1$ and, if desired, also labeled with one or more of the above-defined groups $R_2$, in which process the group or groups $R_1$ are brought to fluorescence, and the fluorescence is measured.

The process according to the invention uses the principle of energy transfer, as discussed above. In comparison with the method according to Dutch patent application No. 8201492, in which compounds labeled exclusively with groups derived from adamantyl-adamantane dioxetane are determined or assayed, the present process has a considerably improved sensitivity. This improvement in sensitivity may be understood by a consideration of the fluorescence of unsubstituted adamantyl-adamantane-dioxetane. Thermal decomposition of this compound yields 2% of singlet and 15% of triplet excited states. Return from the singlet excited state to the ground state yields a photon of light (fluorescence) in 1:200 cases. Return from the triplet excited state to the ground state gives phosphorescence. The fluorescence efficiency of this decomposition reaction is, accordingly, 1:200 ($5 \cdot 10^{-3}$). According to the invention the energy of the singlet excited state is transferred, for example, to the 9,10-diphenyl-anthracyl radical without emission of light. This energy transfer proceeds with an efficiency of almost 100% if the distance between the two molecules is short. As mentioned above, the dipenylanthracyl radical is then in the singlet excited state and will fluoresce by returning to the ground state. The efficiency of this fluorescence is 0.9. This means that the fluorescence emitted on thermal decomposition of the dioxetane is now amplified about 180 times via the fluorescence of the diphenyl-anthracyl radical.

The invention also relates to compounds suitable for use the preparation of organic compounds according to the invention labeled with one or more polycyclic aromatic groups $R_1$. These compounds have the formula $R_1$-Y-X, in which $R_1$ represents a polycyclic aromatic group having at least 3 linearly fused benzene rings, which group can be excited to a fluorescent state by energy transfer from a group or compound in a singlet and/or triplet excited state, Y represents a bivalent organic radical and X represent a reactive group.

The symbol Y represents a bridge radical which, however, may also be absent when, after reaction with the organic compound labeled, at least one atom of the reactive group X remains. That is, the radical $R_1$ should be separated by at least one atom from the organic compound to be labeled. Y may be a bivalent hydrocarbon radical, such as a methylene, ethylene, propylene, butylene or still longer alkylene radical, which may be optionally branched and/or substituted. For example, Y may also be a bivalent hydrocarbon radical which is attached to R₁ via an oxygen or nitrogen atom or via an —NH—CO— group.

The reactive group X may be any desirable reactive group capable of reacting with the organic compound to be labeled. The following groups may be mentioned as examples of reactive groups X: hydroxyl and thiol groups, reactively esterified hydroxyl or thiol groups, halogen atoms, such as chloro, bromo and iodo atoms, acidic groups, such carboxyl groups and sulphonic acid ester groups, oxo groups, acid anhydride groups, amino groups, cyano groups, isocyanate groups, isothiocyanate groups, thiocyanate groups, amidate groups or also metal atoms such as sodium or potassium atoms. The reactive group X may be a magnesium halide group as well.

Among the reactive carboxylic acid ester groups the succinylimid-N-yl-oxycarbonyl radical may be mentioned. This group, with which good results have been obtained, reacts readily with compounds containing an amino group. A reactive group readily reacting with thiol groups is, for example, the maleinimid-N-yl radical.

Particularly suitable for labeling proteins containing one or more free amino groups is the N-hydroxysuccinimide ester of 4-(9,10-diphenylanthracen-2-yl)butyric acid (formula 15).

Further, the invention relates to novel dioxetane compounds suitable for labeling organic compounds with a group of formula 1, that is to say one of possible groups R₂. In forumula 2,

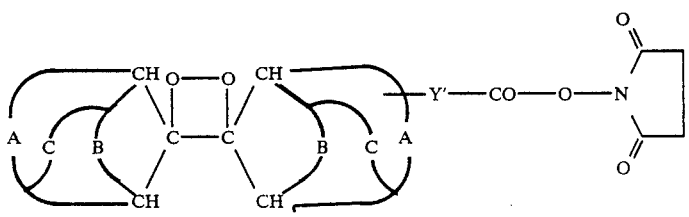

A and B represent alkylene radicals which may be attached to each other via an alkylene radical C, and Y′ represents a direct bond or a bivalent organic radical. The bivalent organic radicals Y′ include the same radicals mentioned above in the definition of Y. Preferably, Y′ is a bivalent hydrocarbon radical attached to the radical of formula 1 via an oxygen atom or via the group —NH—CO—.

A preferred group of compounds of formula 2 has formula 3.

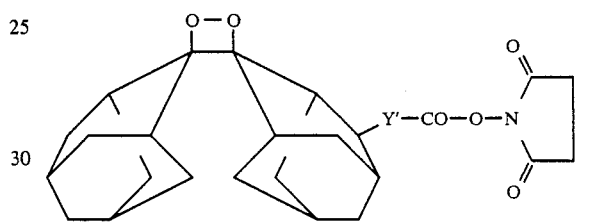

In formula 3, Y′ has the meaning defined above. Compounds particularly well suited for labeling organic compounds containing one or more amino groups are compounds of formula 4

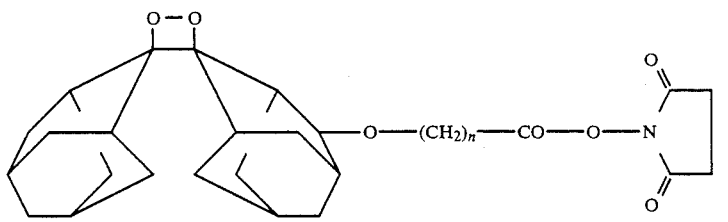

4a: n = 2
4b: n = 3
4c: n = 4 in which n represents an integer of 0–10. Also, good results have been obtained with compounds of formula 5,

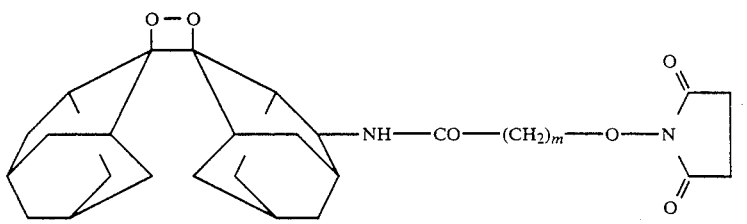

in which m represents an integer of 0–10. A preferred compound is that of formula 6.

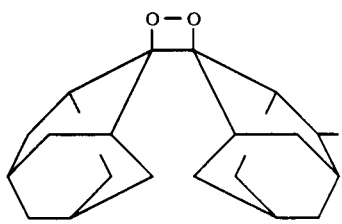 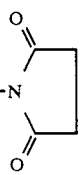

It is also possible to label an organic compound with both a radical $R_1$ and a radical $R_2$, as defined above, by using compounds of formula 16, which also belong to the invention.

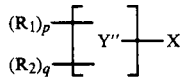                16

In said formula p and q have the value of at least 1, and X represents a reactive group. The reactive group X may have one of the above-mentioned meanings, but in this case X may also represent one or more of the binding sites of an antigen or an antibody. The symbol Y″ represent a bridge group which is at least trivalent and which need have no further requirement than that the groups $R_1$, $R_2$ and X may be attached thereto. An example of a compound of formula 16 is a compound of formula 17,

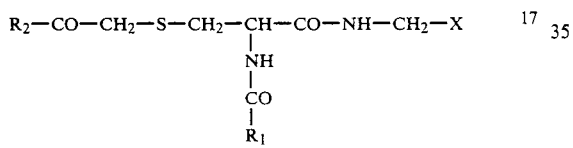      17 in which $R_1$, $R_2$ and X have the above-mentioned meanings. The compound of formula 17 may be prepared by reacting cysteinylglycine (formula 18)

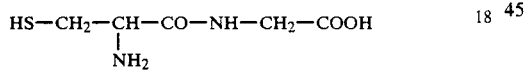    18 with e.g. $R_2$-CO-$Ch_2$-halogen, which reacts preferentially with the mercapto group, and with $R_1$-CO-halogen or another reactive carboxylic acid derivative of $R_1$ which is capable of reacting with the amino group of the cysteinylglycine. The carboxyl group of the product so labeled with $R_1$ and $R_2$ may then be converted into a desired more reactive group.

Generally, an important group of compounds of formula 16 may be prepared by introducing one or more groups $R_1$ and $R_2$ into apolypeptide or protein by reaction with a both a compound of the formula $R_1$-Y-X and a compound of the formula $R_2$Y′-X. The compounds so obtained may be further modified so as to make them suitable for reaction with other molecules which will then be labeled simultaneously with $R_1$ and $R_2$. Thus, a labeled protein may be attached in a known way to another protein, to a hormone or to a small molecule.

The preparation of the compounds of formula $R_1$-Y-X may be effected by conventional procedures well known to those skilled in the art, for example, by introducing the radical -Y-X into a polycyclic aromatic compound $R_1H$. The compound of formula 15 may

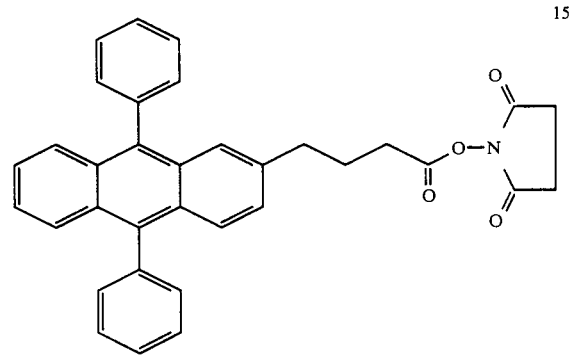

be obtained by esterification of the compound of formula 14 with

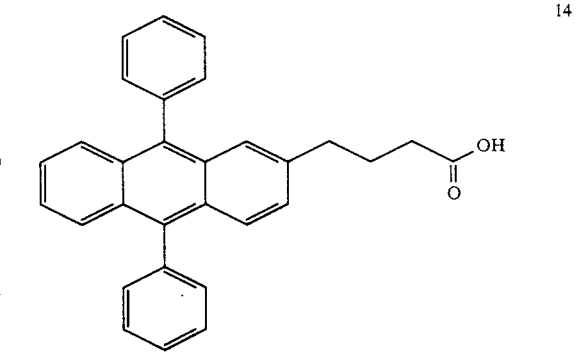

N-hydroxysuccinimide. The compound of formula 14 has been described already in Ann. de Chimie 4, 479–539 (1959). According to this publication the compound of formula 14 is prepared from 9,10-diphenylathracene by reacting the latter compound under Friedel-Crafts conditions with succinic anhydride in the presence of aluminum chloride, which results in the introduction of a succinoyl radical at position 2 of the diphenylanthracene. Then, the carbonyl radical attached to position 2 of the diphenylanthracene is reduced to the methylene group, for example with hydrazine or zinc/HCl, to form the compound of formula 14.

The compounds of formula $R_2$-Y′-X may be prepared by conventional procedures, for example by means of the methods described in Dutch patent application No. 8201492.

The novel compounds of formula 2, especially the novel compounds of formula 3 may be prepared, for example, by using the bromide of formula 7 as a starting material.

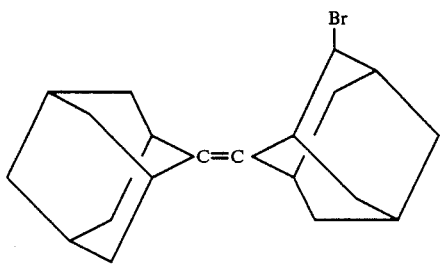

7

The preparation of compounds in which Y' is attache to the epidioxyadamantyl-adamantyl radical via an oxygen atom may be effected by reacting the bromide of formula 7 with an alpha,omega-alkylene glycol, which results in a compound having a hydroxyalkoxy substituent with a terminal hydroxy group, for example the compound of formula 8.

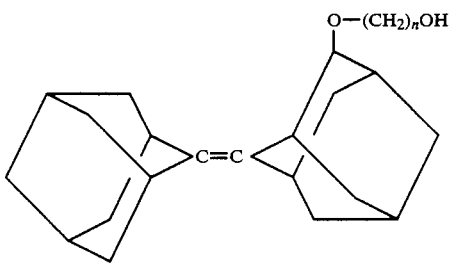

8

8a: n = 3
8b: n = 4
8c: n = 5

The epidioxy group may be introduced into these compounds by conventional procedures using oxygen while irradiating with light in the presence of methylene blue. This results, for example, in a compound of formula 9.

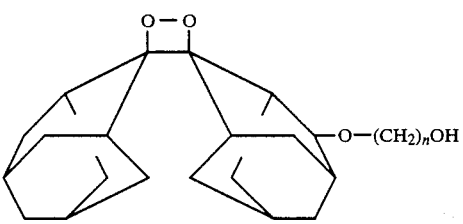

9

9a: n = 3
9b: n = 4
9c: n = 5

The terminal hydroxymethyl radical of this compound may then be oxidized to form the carboxyl group, for example with potassium permanganate, to form for example the compound of formula 10.

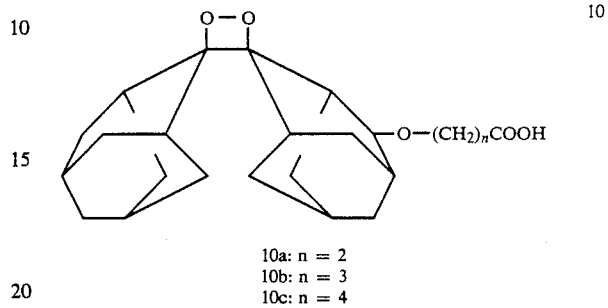

10

10a: n = 2
10b: n = 3
10c: n = 4

The latter compound is then esterified with N-hydroxysuccinimide in the presence of dicyclohexyl carbodiimide to form for example an ester of formula 4.

In this connection it is pointed out that, in all cases, a mixture of isomers is the result of the formation of the dioxetanes from the corresponding unsaturated compounds, for example adamantylidene-adamantanes. Each of the isomers and mixtures thereof are suitable for labeling organic compounds.

Compounds of formula 5 may also be prepared by using the bromide of formula 7 as a starting material, by first replacing the bromide atom with an amino group by reaction with ammonia under pressure. The amino compound of formula 11

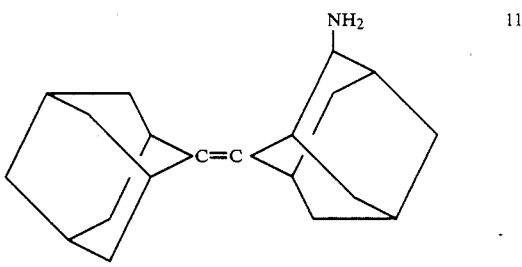

11 is then acylated with succinic anhydride, and the acyl compound of formula 12 so obtained is then esterfied with N-hydroxysuccinimide.

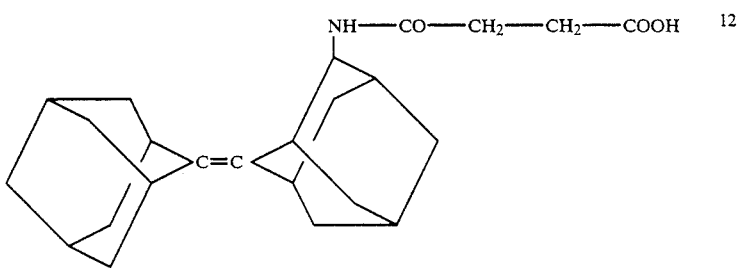

12

Finally, the ester of formula 13 so obtained is converted into the dioxetane of formula 6 by the conventional procedure.

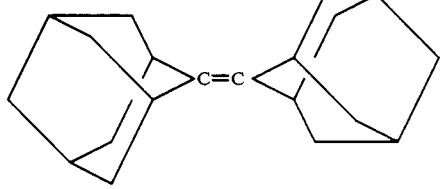 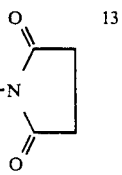

An example of the compounds of formula 16 is the compound described in example XIX. The bovine serum albumin double-conjugate obtained according to example XIX may be attached to an antibody in a know way, for example with a water-soluble carbodiimide. In a similar manner, thyroglobulin was double-conjugated with the compounds of formula 6, and of formula 15, respectively, in a molar ratio of 1:100:100. About 50 molecules of each of the labels were attached to the thyroglobulin. This thyroglobulin-double-conjugate can be coupled by conventional procedures to a further protein, for example by (a) periodate exidation of the sugar radicals of the thyroglobulin, followed by
(b) condensation with one or more amino groups of a protein, and finally
(c) by reduction of the condensate with $NaBH_4$.

Antibodies (sheep-anti-human IgG and goat-anti-carcinoembryonic antigen (goat-anti-CEA); 2 mg/ml) were also labeled with $R_1$ and $R_2$ (in 10% dioxane/100 mM borate buffer pH 8.5, 1 hour reaction time) with various molar ratios of $R_1$ and $R_2$. Sheep-anti-human IgG immunoglobulin gave a maximum molar labeling ratio (during the labeling reaction) of 1:15:20 (antibody:$R_2$:$R_1$). In a double-diffusion technique (Ouchterlony) a precipitation line with human IgG corresponded qualitatively with that of the unconjugated sheep-anti-human IgG. Goat-anti-CEA immunoglobulin conjugated wit $R_1$ and $R_2$ (molar ratio during the reaction 1:20:15) was compared with the same goat-anti-CEA but conjugated with peroxidase. This was carried out in a competition experiment in an enzyme-linked immunosorbent assay (ELISA) technique. It appeared from this experiment that the double-conjugate of g-anti-CEA with $R_1$ and $R_2$ did not show a strong decrease in immunoreactivity.

Immunoglobulin double-conjugates obtained in the same way (g-anti-CEA-$R_1$,$R_2$ and s-anti-IgG-$R_1$, $R_2$) show a specific activity of about 500,000 photon counts per micorgram (measuring efficiency 0.1%). The maximum amplification effect by the 9,10-diphenylanthracene radical is not obtained with immunoglobulins because about 25 $R_1$ radicals per immunoglobulin are necessary for efficient energy transfer from the excited adamantanone to this acceptor. This is due to the relatively short so-called critical distance $R_0$. ($R_0$ is approximately 15 Angstroms according to the theory of Förster; $R_0$ is the distance between donor and acceptor, when the efficiency of the energy transfer is 50%).

In view of what is mentioned above it is very surprising that bovine serum albumin and thyroglobulin (as examples of a relatively small and a relatively large protein) can be saturated with $R_1$ and $R_2$, yet remain soluble in aqueous buffers, and emit a large amount of light (so-called quantum efficiency of both labels does not decrease substantially in heavily conjugated proteins). Further it is very important that the compounds which are labeled with many radicals $R_1$ and $R_2$, are themselves useful as water-soluble labels.

The process for determination or assay of an organic compound labeled with one or more polycyclic aromatic groups $R_1$ having at least three linearly fused benzene rings, which groups $R_1$ may be excited to a fluorescent state by energy-transfer from a group or compound in a singlet and/or triplet excited state, which organic compound is, optionally, also labeled with one or more groups $R_2$ which may be excited to a singlet and/or triplet excited state by thermal energy, is carried out according to the invention by methods known to those skilled in the art for effecting qualitative or quantitative photometry. When a compound containing one or more groups $R_1$ together with one or more groups $R_2$ is to be determined or assayed, the compound has to be heated so as to excite the group or groups $R_2$ into a singlet and/or triplet excited state. The groups $R_2$ transfer their energy to the groups $R_1$, and this results in fluorescence of the groups $R_1$. This fluorescence is measured in the usual way. In principle, the apparatus consists of an oven, the temperature of which may be set to a predetermined value and in which a sample may be heated, for example on a plate of glass or of a suitable plastic, for example polytetrafluoroethylene. A photodetector, e.g. a multiplier phototube is positioned as near as possible to the sample, but separated by a heat filter. The emitted light may also be transmitted to the photomultiplier via an optical glass fibre cable. After insertion of the sample into the oven the temperature of the oven is raised to about 250° C. in a few seconds. The thermal decomposition of the 1,2-dioxetane radicals will then take place within about 20 seconds. The signal of the photomultiplier is coupled to a discriminator/photon-counter via a preamplifier. The discriminator/photon-counter integrates the signal over a short period of time, for example 2 seconds. These integrated values are fed to a computer. The highest integrated value (over 2 seconds) and also the total integrated value (over about 30 seconds) are linearly proportional to the number of radicals $R_2$ over a very broad range of concentration. The background signal may be kept extremely low by removing the oxygen (as far as possible) from the zone in which the sample is heated, for example by flushing with nitrogen or by working in vacuum.

The following examples illustrate the invention but are not intended to be limiting.

13 …

EXAMPLE

Preparation of
4-eq.-(3-hydroxypropoxy)adamantylidene-adamantane
(formula 8a)

Ten grams of 4-eq.-bromoadamantylidene-adamantane of formula 7 was mixed with 250 ml of dry propanediol-1,3, and the mixture was refluxed for 2.5 hours. The reaction mixture was poured into 500 ml water. Extraction with dicloromethane (2×259 ml), washing of the combined extracts with 250 ml of water, drying with MgSO$_4$, filtration and high vacuum evaporation gave 10.0 g of spectroscopically pure 4-eq.-(3-hydroxypropoxy)adamantylidene-adamantane (formula 8a) in the form of a yellow oil.

Analytically pure material was obtained after distillation in a rotating evaporator (250° C., 0.002 mm Hg): 9.0 g (91%).

Analysis: calculated for $C_{23}H_{34}O_2$:80.63% C; 10.02% H. Found: 80.52% C; 9.95%H.

IR spectrum (neat): 3400 (s), 2900 (s), 1450 (s), 1100 (br) cm$^{-1}$.

EXAMPLE II

Preparation of
4eq.-(4-hydroxybutoxy)adamantylidene-adamantane
(formula 8a)

The process of Example I was repeated with the difference that 250 ml of dry butanediol-1,4 was used instead of propanediol-1,3. The product, 4-eq.-(4-hydroxybutoxy)adamanytlidene-adamantane (formula 8b) was obtained in crude form as a yellow oil (11.0 g), which was purified by column chromatography on Al$_2$O$_3$ with dichloromethane as the eluent. In this way, 9.94 g (97%) of spectroscopically pure product was obtained in the form of a colorless oil.

IR spectrum (neat): 3350 (s), 2900 (s), 1450 (s), 1100 (br) cm$^{-1}$.

$^1$H-NMR spectrum (CDCl$_3$, TMS): delta 3.8–3.1 (m, 5H); 2,85 (br, 4H); 2.3–1.0 (m, 27H).

$^{13}$C-NMR spectrum (CDCl$_3$): delta 135.6; 130.8 82.3; 67.5; 62.5; 39.6; 39.4; 39.0; 37.0; 36.8; 35.4; 32.9; 32.2; 31.9; 31.5; 31.0; 30.8; 30.5; 28.3; 27.5; 27.3.

Mass spectrum: M+-peak at m/e 356 (20%); 284; 268; 135; 79.

Exact mass: expected 356.272; experimental: 356.273.

EXAMPLE III

Preparation of
4-eq.-(5-hydroxypentoxy)adamantylidene-adamantane
(formula 8c)

The process of Example I was repeated with the difference that 250 ml of dry pentanediol-1,5 was used instead of propanediol-1,3. The product, 4-eq.-(5-hydroxypentoxy)adamantylidene-adamantane (formula 8c) which was obtained in crude form as a yellow oil, was purified by column chromatography on Al$_2$O$_3$ with dichloromethane as the eluent. In this way 9.0 g (85%) of a colorless product was obtained.

IR spectrum (neat): 3400 (s), 2900 (s), 1445 (s) 1100 (br) cm$^{-1}$.

$^l$H-NMR spectrum (CDCl$_3$, TMS): delta 3.8–3.1 (m, 5 H); 2.9 (br, 4 H); 2.45 (s, 1 H); 2.6–1.0 (m, 28 H).

$^{13}$C-NMR spectrum (CDCl$_3$): delta 135.2; 130.9; 81.7; 67.1; 62.1; 39.3; 38.9; 37.0; 36.7; 35.4; 32.8; 32.1 31.8; 31.5; 30.8; 29.6; 28.2; 27.4; 22.4.

Mass spectrum: M+-peak at m/e 370 (55%); 268; 135; 79.

Exact mass: expected 370.287; experimental 370.288.

EXAMPLE IV

Preparation of
4-eq.-(3-hydroxypropoxy)-2,2'-epidioxy-2,2'-adamantyl-adamantane (formula 9a)

The compound of formula 8a (4 g) was dissolved in dichloromethane (700 ml). Methylene blue (20 mg) was then added. The mixture so obtained was irradiated with a sodium lamp (Philips SON 160 W), which was provided with a reflector and was positioned at a short distance from the solution. During the irradiation, oxygen was led through the solution. The irradiation and the oxygen treatment were continued for 7 hours, and solvent was added from time to time. The temperature of the solution rose to about 40° C. After the irradiation the solvent was evaporated and the residue was chromatographed on a column of Al$_2$O$_3$ with dichloromethane as the first and ethyl acetate as the second eluent. The fraction containing the compound of formula 9a was treated with decolorizing carbon and evaporated. In this way the compound of formula 9a was obtained as a mixture of two isomers in the form of a colorless oil (4.1 g, 94%).

IR spectrum (neat): 3450 (s), 1455 (s), 1100 (br) cm$^{-1}$.

$^l$H-NMR spectrum (CDCl$_3$, TMS): delta 3.82 (t, J=11 Hz, 2 H), delta 3.68 (t, J=11 Hz, 2 H); delta 3.15 (br, 1 H), delta 2.85 (br, 1 H), delta 2.65 (br, 4 H), delta 2.3–1.2 (m, 24 H).

$^{13}$C-NMR spectrum (CDCl$_3$): delta 96.2; 96.0; 95.4; 77.7; 76.9; 67.5; 67.0; 62.2; 61.9; and 22 peaks between delta 39 and 25.4.

Mass spectrum: Fragments M=150 and M=224.

Exact mass of largest fragment: expected 224.141; found 224.143. No M+ at m/e 374.

EXAMPLE V

Preparation of
4-eq.-(4-hydroxybutoxy)-2,2'-epidioxy-2,2'-adamantyl-adamantane (formula 9b)

The compound of formula 8b (9.8 g) was treated as in Example IV. The compound of formula 9b was obtained as a mixture of two isomers in the form of a colorless oil (9.4 g; 88%).

IR spectrum (neat): 3400 (s), 2900 (s), 1450 (s), 1100 (br) cm$^{-1}$.

$^1$H-NMR spectrum (CDCl$_3$, TMS): delta 3.75–3.2 (m, 5 H); delta 3.0–2.4 (m, 5 H); delta 2.3–1.0 (m, 26 H).

$^{13}$C-NMR spectrum (CDCl$_3$): delta 96.1;95.9; 95.3; 77.3; 76.5; 67.8; 67.6; 62.3; 62.2; and 25 peaks between delta 36.9 and 25.4.

Mass spectrum: Fragments m/e=238 and 150 (100%).

Exact mass of largest fragments expected for $C_{14}H_{22}O_3$: 238.157; experimental: 238.158.

EXAMPLE VI

Preparation of 4-eq.-(5-hydroxypentoxy)-2,2'-ipidioxy-2,2'-adamantyladamantane (formula 9c)

The compound of formula 8c (4 g) was treated as in Example IV. The compound of formula 9c was obtained as a mixture of two isomers in the form of a colourless oil (3.6 g; 83%).

IR spectrum (neat): 3450 (s), 2950 (s), 1460 (s), 1100 (br) cm$^{-1}$.

$^1$H-NMR spectrum (CDCl$_3$): delta 3.8–3.2 (m, 5 H); 3.0–2.4 (m, with peaks at delta 2.80 and 2.62; 5 H); 2.3–1.0 (m, 28 H).

$^{13}$C-NMR spectrum (CDCl$_3$): delta 96.3; 96.0; 95.6; 95.5; 77.2; 76.1; 67.6; 62.6; 62.5; and peaks between delta 37.3 and 22.3.

Mass spectrum: Fragments at m/e=252 and 150 (100%), further 121 and 79.

Exact mass: Fragment 252: expected 252.173; found 252.174.

EXAMPLE VII

Preparation of 3-(2,2'-epidioxy-2,2'-adamantyl-adamant-4-eq.-yl-oxy)-propionic acid (formula 10a)

The compound of formula 9a (mixture of two isomers; 0.60 g; 160 mmole) was dissolved in acetic acid (1.8 cm$^3$). To this solution 0.38 g KMnO$_4$ was added slowly with stirring at room temperature. After this, the mixture was stirred for 4 hours at room temperature. Then, water (50 cm$^3$) and a saturated solution of sodium hydrogen sulphite in water (20 cm$^3$) were added and the solution was extracted with 50 cm$^3$ of dichloromethane. The organic phase was separated, washed with water (2×50 cm$^3$), dried with magnesium sulphate, filtered and evaporated. This resulted in a colourless oil. This was dissolved in pentane/ether 1:2 (50 cm$^3$), and HN$_3$ gas was led through the solution; the compound of formula 10a precipitated as the ammonium salt in the form of an oil. The supernatant was decanted and the residue was washed with n-pentane (2×20 cm$^3$). Dichloromethane (50 cm$^3$) was added and the solution was washed with 2N HCl (20 cm$^3$) and then with water (50 cm$^3$). The solution was then dried with MgSO$_4$ and filtered. After evaporation of the solvent and drying of the residue under high vacuum the residue was the spectroscopically pure compound of formula 10a as a colourless viscous oil (0.30 g; 48% mixture of two isomers).

IR spectrum (neat): 3700–2400 (s); 2900 (s), 1705 (s), 1460 (m), 1100 (m) cm$^{-1}$.

$^1$H-NMR spectrum (CDCl$_3$, TMS): delta 9.3 (br, 1 H), delta 3.75 (t, J=6 Hz, 2 H), delta 3.6 (br, 1 H); 3.0–2.4 (m, 6 H), 2.3–1.0 (m, 22 H).

$^{13}$C-NMR spectrum (CDCl$_3$): delta 177.2; 96.2;96.0; 95.4; 77.6; 76.6; 62.9; 62.8; and 22 signals between 36.9 and 25.4.

Mass spectrum: Fragments m/e=238 (15%) and 150 (50%), further 222, 165 and 79 (100%).

Exact mass of fragment 238: expected 238.120; found 238.121. No M$^+$-peak.

EXAMPLE VIII

Preparation of 4-(2,2'-epidioxy-2,2'-adamantyl-adamant-4-yl-oxy)-butyric acid (formula 10b)

The compound of formula 9b (mixture of two isomers; 2.0 g; 5.15 mmole) was oxidized as in Example VII (acetic acid 5 cm$^3$; KMnO$_4$ 1.2 g; reaction time 3 hours), and purified in a similar way. After evaporation of the dichloromethane the compound of formula 10b was obtained as a colourless viscous oil (1.58 g; 76%; mixture of two isomers).

IR spectrum (neat): 3700–2400 (s), 2950 (s), 1705 (s), 1455 (m), 1105 (s) cm$^{-1}$.

$^1$H-NMR spectrum (CDCl$_3$, TMS): deltas 8.3 (br, 1H), 3.47 (t, J=6 Hz, 2 H), 3.4 (br, 1 H), 2.9–1.0 (m, with peaks at delta 2.8; 2.6; 2.5; 2.4; 1.85; 30 H).

$^{13}$C-NMR spectrum (CDCl$_3$): delta 179.3; 96.2; 96.0; 95.5; 77.3; 76.4; 66.6; 66.3; and 23 signals between 37.0 and 25.0.

Mass spectrum: Fragments with m/e=252 and 150 (100%), further 165 and 79.

Exact mass fragment 252: expected 252.136; found 252.138. No M$^+$-peaks.

EXAMPLE IX

Preparation of 5-(2,2'-epidioxy-2,2'-adamantyl-adamant-4-eq.-yl-oxy)-valeric acid (formula 10c The compound of formula 9c (mixture of two isomers; 3.6 g; 9.0 mmole) was oxidized as in example VII (acetic acid 10 cm$^3$; KMnO$_4$ 2.0 g; reaction time 3 hours) and purified in the same way. After evaporation of the dichloromethane the compound of formula 10c was obtained as a colourless viscous oil (2.4 g; 65% mixture of two isomers).

IR spectrum (neat): 3600–2500 (s); 2900 (s), 1710 (s), 1460 (m), 1100 (m) cm$^{-1}$.

$^1$H-NMR spectrum (CDCl$_3$, TMS): delta 9.0 (br, 1 H; delta 3.6–3.2 (M, 3 H); delta 3.0–1.0 (m, with peaks at delta 2.78; 2.65; 2.38; 2.28; 1.90; and 1.70; 32 H).

$^{13}$C-NMR spectrum (CDCl$_3$): delta 1.79.0; 96.4; 96.1; 95.7; 95.5; 77.3; 76.4; 67.2; 40 peaks between 37.2 and 21.6.

Mass spectrum: Fragments with m/e=266 and 150 (70%), further 121, 101, 79.

Exact mass of fragment 266: expected 266.152; found 266.154. No M$^+$-peaks found.

EXAMPLE X

Preparation of the N-hydroxysuccimimide ester of 3-(2,2'-epidioxy-2,2'-adamantyl-adamant-4-eq.-yl-oxy)-propionic acid (formula 4a)

The compound of formula 10a (mixture of two isomers; 1.85 g; 4.8 mmole) was dissolved in dry dioxane (10 cm$^3$). Dicyclohexyl carbodiimide (1.1 g; 5 mmole) and dry N-hydroxysuccinimide (480 mg, 4.85 mmole) were added to the mixture. The mixture was stirred at room temperature for 16 hours with exclusion of humidity. The suspension was filtered and the solvent was evaporated under vacuum. The residue was washed with dry n-hexane (50 cm$^3$) and then dissolved in dry dichloromethane (50 cm$^3$). A insoluble portion was removed by filtration over a short column of sea-sand. Then the solvent was evaporated under high vacuum. The compound of formula 4a was the residue in the form of a white foam (mixture of two isomers; 2.2 g, 95.5; spectroscopically pure).

IR spectrum (neat): 2900 (s), 1810 (m), 1775 (m), 1730 (s), 1460 (m), 1200 (m) cm$^{-1}$.

$^1$H-NMR spectrum (CDCl$_3$), TMS): delta 3.83 (t, J=7 Hz, 2 H); 3.7 (br, 1 H); 3.1-2.4 (m, with peak at delta 2.85; 10 H); 2.3≧1.0 (m, 22 H).

$^{13}$C-NMR spectrum (CDCl$_3$): delta 168.9; 166.5; 95.9; 95.6; 95.1; 77.6; 62.1; and 19 peaks between delta 36.7 and 25.1.

Mass spectrum: Fragments m/e=335 and 150, further 165, 149, 121 (100%).

Exact mass of fragment 335: expected 335.137; found 335.138. No M+-peak.

EXAMPLE XI

Preparation of the N-hydroxysuccinimide ester of 4-(2,2'-epidioxy-2,2'adamantyl-adamant-4-eq.-yl-oxy)-butyric acid (formula 4b)

The compound of formula 10b (mixture of two isomers; 210 mg.; 0.52 mmole) was esterified with N-hydroxysuccinimide corresponding to the method of Example X. After working up as in Example X the compound of formula 4b was obtained as a residue in the form of a colorless viscous oil (yield 90%, 235 mg; spectroscopically pure; mixture of two isomer).

IR spectrum (neat): 2920 (s), 1810 (m), 1780 (m), 1735 (s), 1460 (m), 1200 (m), 1070 (s) cm$^{-1}$.

$^1$H-NMR spectrum (CDCl$_3$, TMS): delta 3.50 (t, J=6 Hz, 2 H); 3.4 (br, 1 H); 2.80 (s, 4 H); 2.65 (m, 4 H); 2.3-1.0 (m, 26 H).

$^{13}$C-NMR spectrum (CDCl$_3$): delta 169.0; 168.4; 96.2; 96.0; 95.5; 77.3; 65.7; 65.5; and peaks between delta 37.0 and 24.5.

Mass spectrum: Fragments m/e=349 (6%) and 150 (35%), further 165, 149, 121 (100%), 79.

Exact mass of fragment 349: expected 349.153; found 349.152. No M+-peak.

EXAMPLE XII

Preparation of the N-hydroxysuccinimide ester of 5-(2,2'-epidioxy-2,2'-adamantyl-adamant-4-eq.-yl-oxy)-valerianic acid (formula 4c).

The compound of formula 10c (mixture of two isomers; 2.0 g; 4.8 mmole) was esterified with N-hydroxysuccinimide corresponding to the method of Example X. After working up as in Example X the compound of formula 4c was obtained as a residue in the form of a foamy which substance (95%; 2.35 g; spectroscopically pure; mixture of two isomers).

IR spectrum (neat): 2900 (s), 1805 (m), 1775 (m), 1730 (s), 1460 (m), 1200 (s), 1060 (s) cm$^{-1}$.

$^1$H-NMR spectrum (CDCl$_3$): delta 3.50 (t, J=6 Hz, 2 H); 3.4 (br, 1 H); 2.80 (s, 4 H); 2.65 (m, 4 H); 2.3-1.0 (m, 28 H).

$^{13}$C-NMR spectrum (CDCl$_3$): delta 168.9; 168.3; 168.2; 96.1; 95.8; 95.4; 95.3; 77.2; 76.2; 66.9; 66.8; further peaks between delta 37.0 and 21.5.

Mass spectrum: fragments m/e 363 (5%) and 150 (50%), further 165, 149, 121 (100%), 79.

Exact mass of fragment 363: expected 363.168; found 363.169. No M+-peak.

EXAMPLE XIII

Preparation of 4-eq.-amino-adamantylidene adamatane (formula 11)

The compound of formula 7 (7 g, 0.020 mole) was mixed with dry dioxane (75 ml) in a stainless steel cylinder. Then liquid NH$_3$ was introduced (250 ml) until 4/5 of the cylinder was filled. After cooling the temperature of the cylinder was raised to 70° C. and kept at that temperature in a Carius oven. After 3-16 hours the cylinder was cooled with liquid N$_2$, opened and (after excess NH$_3$ was evaporated), the contents was poured into 1N NaOH (100 ml). The product was taken up into either (250 ml), and the ether solution was separated and washed with H$_2$O (3×200 ml). The organic phase was dried with MgSO$_4$, filtered and evaporated. The residue was the compound of formula II (spectroscliclly pure) in the form of a white solid (5.70 g, 95%).

EXAMPLE XIV

Preparation of N-adamantylidene-adamant-4-eq.-yl-succinic acid monoamide (formula 12)

A solution of the compound of formula 11 (9 g; 32 mmole) in absolute ethanol (75 cm$^3$) was added to a solution of succinic anhydride (3.2 g; 32 mmole) in absolute ethanol (150 cm$^3$). The mixture was stirred for 18 hours at room temperature. Then the mixture was cooled to 0° C. and the product was filtered and washed with cold ethanol (100 cm$^3$). The compound of formula 12 was obtained as a white solid (12.2 g; 90%); melting point 253°-256° C).

IR spectrum (KBr): 3400 (m), 3300-2500 (s), 2900 (s), 1720 (s), 1640 (s) and 1550 (s) cm$^{-1}$.

$^1$H-NMR spectrum (DMSO-d$_6$): delta 7.5 (br, 1 H); 3.6 (m, 1 H); 2.7 (m, 4 H); 2.3 (br, s, 4 H) and resonance to delta 1.0 (22 H).

$^{13}$C-NMR spectrum (DMSO-d$_6$): delta 174.0; 170.5; 134.4; 131.5; 53.9; 37.9; 36.7; 35.2; 32.7; 31.7; 31.5; 31.5; 31.4; 30.6; 30.4; 30.2; 29.4; 27.8; 27.0.

Mass spectrum: M+ at m/e 383 (100%), further 365, 283, 266.

Exact mass: expected at 383.246; found 383.244.

EXAMPLE XV

Preparation of 4-eq.-(2-succinimid-N-yl-oxycarbonyl)ethyl-carbonyl-amino)-2,2'-adamantylidene adamantane (formula 13)

The compound of formula 12 (1.65 g; 4.3 mmole) was dissolved in anhydrous dimethylformamide (50 cm$^3$) with heating. After cooling to room temperature dicyclohexylcarbodiimide (900 mg; 4.35 mmole) was added. After stirring for 10 minutes N-hydroxysuccinimide (660 mg; 5.75 mmole) was added and then the mixture was stirred at room temperature under exclusion of humidity during 16 hours. A small amount of precipitate which ws formed was removed by filtration. The solvent was evaporated under high vacuum. The residue was washed with n-hexane (2×50 cm$^3$) and then dissolved in dichloromethane (50 cm$^3$). Turbidity of the solution was removed by filtration through a short column of sea sand. Then the solvent was removed under high vacuum and the compound of formula 13 was obtained as a residue in the form of a white solid (2.06 g, 100%); melting point: 191°-194° C. (ethyl acetate).

IR spectrum (KBr): 3400 (m, NH), 2900 (s), 1805 (m), 1770 (m), 1720 (s), 1660 (m), 1200 (m), 1060 (m) cm$^{-1}$.

$^1$H-NMR spectrum (CDCl$_3$, TMS, 200 MHz)): delta 5.95 (d, J=7 Hz; 1 H); 3.9 (m, 3 H); 3.02 (t,J=7.5 Hz; 2 H); 2.87 (m, 4 H); 2.83 (s, 4 H); 2.63 (t, J=7.5 Hz; 2 H); 2.2–1.0 (m, 22 H).

$^{13}$C-NMR spectrum (CDCl$_3$): delta 168.8; 168.3; 136.0; 130.4; 54.3; 39.4; 39.0; 37.6; 37.1; 35.2; 33.8; 33.2; 32.2; 32.0; 31.6; 31.2; 30.9; 330.6; 28.3; 28.2; 27.3; 26.8; 25.4; 24.7.

Mass spectrum: M+-peak at m/e=480, further 365 (100%) and 267.266.

Exact mass expected at 480.262; found 480.263.

EXAMPLE XVI

Preparation of 4-eq.-[2-(succinimic-N-yloxycarbonyl)ethyl-carbonylamino]-2,2'-epidioxy-2,2'-adamantyl adamantane (formula 5a)

The compound of formula 13 (800 mg, 1.57 mmole) was disssolved in dichloromethane (200 cm$^3$) together with methylene blue (5 mg), and the solution was irradiated and saturated with oxygen in a way described in Example IV for 5 hours. Decolorizing carbon (200 mg) was added to the solution; after stirring, the solution was filtered and the solvent was evaporated under vacuum. After stirring with n-pentane (50 cm$^3$) and evaporation of the solvent the compound of formula 5a, a mixture of two isomers, remained as a white solid (750 mg, 89%). The material so obtained was spectroscopically pure and was used as such for coupling reactions.

Melting point 50°–95° C.

IR spectrum (KBr): 3400 (br, NH), 2950 (s), 1810 (m), 1780 (m), 1730 (s), 1650 (m), 1540 (m), 1200 (m), 1080 (m) cm$^{-1}$.

$^1$H-NMR spectrum (CDCl$_3$, TMS, 200 MHz): delta 6.20 (d, J=8 Hz; ½ H); 6.00 (d, J=8 Hz; ½ H); 4.25 (m, ½ H); 4.16 (m, ½ H); 300 (t, J=8 Hz; 2 H); 2.83 (s, 4 H); 2.65 (t, J=8 Hz); 2.78–2.5 (m, 6 H); 2.2–1.2 (m, 22 H).

$^{13}$C-NMR spectrum (CDCl$_3$): delta 169.2; 169.1; 168.9; 168.3; 168.2; 96.0; 95.7; 95.4; 95.3; 49.5; 48.6; signals between 39.4 and 24.7.

Mass spectrum: Fragments m/e 362 and 150; further 247, 219, 149, 100, 79.

Exact mass of fragment 362: expected 362.148; found 362.150.

EXAMPLE XVII

Preparation of N-hydroxysuccinimide ester of 4-(9,10-diphenylanthracen-2-yl)butyric acid (formula 15)

4-(9,10-diphenylanthracen-2-yl)butyric acid of formula 14 (prepared according Ann. de Chimie 4, 479–539 (1959)) was esterified with N-hydroxysuccinimide in the way described in Example X. The compound of formula 15 was obtained as an orange-yellow solid (100% yield, spectroscopically pure), and was used as such for coupling reactions.

IR spectrum (KBr): 2950 (w), 1805 (m), 1770 (m), 1720 (s), 1620 (m), 1200 (m), 1060 (m), 745 (m), 695 (m) cm$^{-1}$.

$^{13}$C-NMR spectrum (CDCl$_3$): delta 168.9; 168.2; 138.9; 137.0; 136.8; 136.2; 131.1; 129.9; 129.7; 129.4; 128.6; 128.2; 127.9; 127.2; 126.7; 126.4; 125.0; 124.8; 124.6; 34.7; 29.9; 25.6; 25.3.

Mass spectrum: M+-peak at m/e=513 (100%), further 497, 416, 399, 356, 343.

Exact mass: expected 513.194; found 513.192.

EXAMPLE XVIII

Coupling of the Compound of Formula 4c to a Protein d

A solution of the compound of formula 4c (175 mg) in dioxane (33 cm$^3$) was added to a solution of bovine serum albumin (1 g) in borate buffer (0.1M; pH 8.5; 133 cm$^3$). After two hours reaction time the clear mixture was first dialyzed against dioxane (H$_2$O (1:4), (2 dm$^3$)) and then against distilled water (4×2 dm$^3$). After freeze-drying of the protein with BSA was obtained as a white solid (1 g). This material, which contains about 10 labels per molecule of protein, which was determined by means of amino group titration according to Habeeb (Anal. Biochem. 14, 328–36 (1966)) gives 2·10$^6$ photon counts per microgram protein in an apparatus for thermochemiluminescence with measuring efficiency of about 0.1%. The blank value of the measurement is less than 100 photon counts.

EXAMPLE XIX

A solution of bovine serum albumin-conjugate (0.2 mg) obtained according to Example XVIII, but having a molar ratio of BSA to the compound of formula 4c of 1:25, in borate buffer (100 mM, pH 8.5; 0.2 cm$^3$) was mixed with a solution of the compound of formula 15 (0.5 mg) in acetone (0.1 cm$^3$). After 30 minutes reaction time the conjugate of BSA, compound of formula 4c and compound of formula 15 was purified by dialysis. This material, dissolved in a 1% solution of BSA in distilled water, gives 40 times the number of photon counts as the starting material used in this example, in the entire range of concentration (100 pg/ml to 1 μg/ml; from this, 1 μl was taken for a measurement).

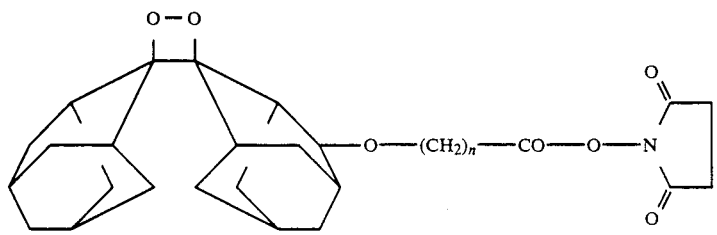
wherein n represents an integer of 0–10.
33. The compound of claim 32 wherein n represents an integer 2, 3 or 4.
34. A compound of claim 28 having the formula
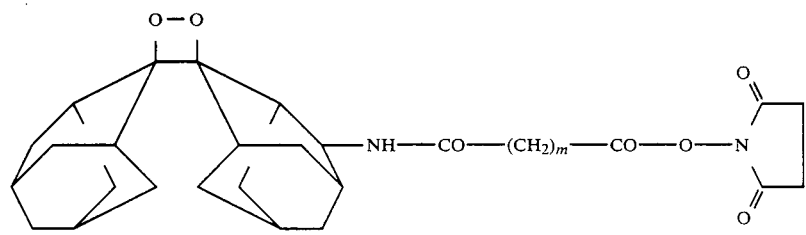
wherein m represents an integer of 1–10.
35. A compound of claim 28 having the formula
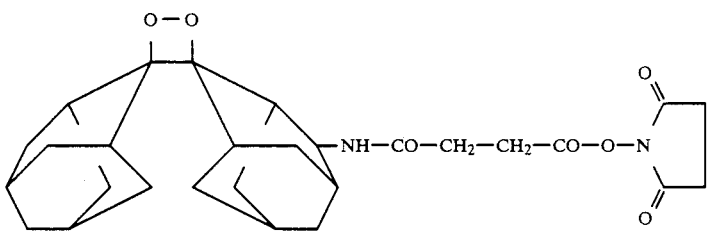

What is claimed is:

1. A doubly labeled organic compound comprising a compound to be labeled, a fluorescent label covalently bonded thereto, said fluorescent label being a polycyclic aromatic radical R$_1$ having at least three linearly fused benzene rings, said polycyclic aromatic radical having a fluorescent electronic excited state to which it can be excited by energy transfer from another radical having an electronic excited state, and an excitation label R$_2$ which comprises an organic radical having an electronic excited state to which it can be excited by absorption of thermal energy, wherein R$_1$ represents a radical derived from a compound selected from the group consisting of rubrene, perylene, 9, 10-dibromo anthracene, 9, 10-dichloro anthracene and 9, 10-diphenyl anthracene and wherein R$_2$ represents an organic radical of the formula

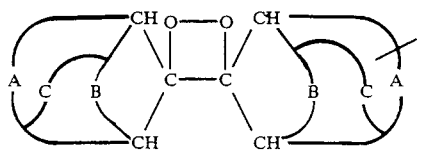

which A and B represent alkylene radicals which may be connected to each other via an optional alkylene radical C.

2. The labeled compound of claim 1 wherein said compound to be labeled is selected from the group consisting of proteins, steroids and fatty acids.

3. The labeled compound of claim 2 wherein said protein is an immunoreactive protein.

4. The labeled compound of claim 3 wherein said protein is an antigen or an antibody.

5. The labeled compound of claim 1 wherein said labeled compound is an imunological complex.

6. The labeled compound of claim 1, wherein alkylene radicals A and B each contain 2–5 carbon atoms.

7. The labeled compound of claim 6 wherein said alkylene radical C contains 1–4 carbon atoms.

8. The labeled compound of claim 1, wherein radical $R_2$ is the 2,2'-epidiosy-2,2'-adasmantyladamant-4-eq.-yl radical.

9. A method of detecting a fluorescent labeled organic compound of claim 1, said method comprising exciting said polycyclic aromatic radical to its fluorescent electronic excited state, whereby it emits fluorescece, and detecting the emitted fluorescence.

10. The method of claim 9 wherein said polycyclic aromatic radical is excited to its fluorescent electronic excited state by energy transfer from another radical having an electronic excited state.

11. The method of claim 10 wherein said other radical is generated by a chemical reaction in the presence of said labeled organic compound.

12. The method of claim 11 wherein said chemical reaction is the reaction of an oxalic acid derivative with hydrogen peroxide.

13. A method of detecting a labeled organic compound of claim 1 comprising heating said compound to a temperature at which said excitation label $R_2$ is excited to its electronic excited state by absorption of thermal energy.

14. A compound of the formula $R_1$—Y—X, in which $R_1$ is a polycyclic aromatic radical having at least three linearly fused benzene rings, said polycyclic aromatic radical having a fluorescent electronic state to which it can be excited by energy transfer from a donor radical having an electronic excited state, Y represents a direct bond or a bivalent organic radical, and X represents a reactive group selected from a succinylimid-N-yl-oxycarbonyl group or a maleinimid-N-yl group.

15. The compound of claim 14 wherein $R_1$ is the 9,10-diphenylanthracyl group.

16. The compound of claim 14, wherein X represents an acid halide group.

17. The compound of claim 14, in which X represens a succinylimid-N-yl-oxycarbonyl group.

18. The compound of claim 14, in which X represents maleinimid-N-yl-group.

19. The compound of claim 14, in which Y represents a biavalent hydrocarbon radical.

20. The compound of claim 14, in which Y represents a bivalent hydrocarbon radical attached to $R_1$ via an oxygen or nitrogen atom.

21. The compound of claim 14, in which Y represents a bivaslent hydrocarbon radical attached to $R_1$ via an —NH—CO— group.

22. The compound of claim 14 which is the N-hydroxysuccinimide ester of 4-(9,10-diphenylanthracen-2-yl) butyric acid.

23. A compound of the formula

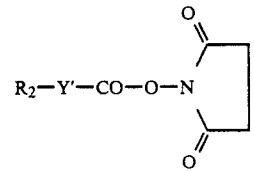

wherein $R_3$ has the formula

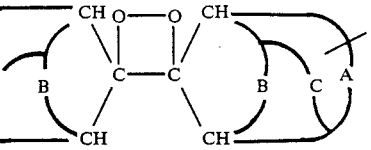

wherein A and B represent alkylene radicals, is an optional alkylene radical which may connect A and B, and Y' represents a direct bond or a bivalent organic radical.

24. The compound of claim 23, wherein said bivalent organic radical Y' is a bivalent hydrocarbon radical.

25. The compound of claim 23, wherein said bivalent organic radical Y' is a direct bond or a bivalent hydrocarbon radical attached to the radical $R_2$ via an oxygen or nitrogen atom.

26. The compound of claim 23, wherein said bivalent hydrocarbon radical Y' is attached to the radical $R_2$ via an —NH—CO— group.

27. The compound of claim 23, wherein Y' has the formula —NH—CO—$CH_2$—$CH_2$—.

28. The compound of claim 23 having the formula

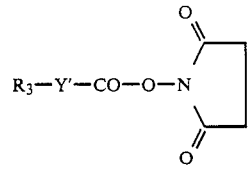

wherein $R_3$ had the formula

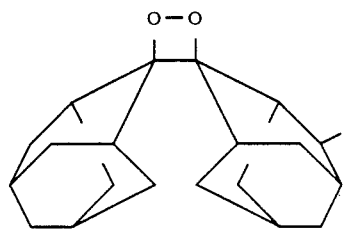

in which Y' is a bivalent organic radical.

29. The compound of claim 28, wherein said bivalent organic radical Y' is a direct bond or a bivalent hydrocarbon radical attached to the radical $R_3$ via an oxygen or nitrogen atom.

30. The compound of claim 28, wherein said bivalent hydrocarbon radical Y' is attached to the radical $R_3$ via an —NH—CO— group.

31. The compound of claim 28, wherein Y' has the formula —NH—CO—$CH_2$—$CH_2$—.

32. The compound of claim 28 having the formula